US00PP25582P2

(12) United States Plant Patent
Isobe

(10) Patent No.: US PP25,582 P2
(45) Date of Patent: May 26, 2015

(54) ***DIANTHUS* PLANT NAMED 'SUNNADE PINTATSU'**

(50) Latin Name: *Dianthus×hybrida*
Varietal Denomination: Sunnade Pintatsu

(71) Applicant: Yasuko Isobe, Shiga (JP)

(72) Inventor: Yasuko Isobe, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 156 days.

(21) Appl. No.: 13/986,655

(22) Filed: May 21, 2013

(51) Int. Cl.
*A01H 5/00* (2006.01)

(52) U.S. Cl.
USPC ..... Plt./277

(58) Field of Classification Search
USPC ..... Plt./273, 277
See application file for complete search history.

*Primary Examiner* — Susan McCormick Ewoldt
(74) *Attorney, Agent, or Firm* — C. A. Whealy

(57) ABSTRACT

A new and distinct cultivar of *Dianthus* plant named 'Sunnade Pintatsu', characterized by its upright, outwardly spreading and mounding plant habit; vigorous growth habit; freely branching habit; freely flowering habit; and large single flowers with vivid red purple-colored fringed petals; flowers positioned above and beyond the foliar plane on strong peduncles.

1 Drawing Sheet

Botanical designation: *Dianthus×hybrida*.
Cultivar denomination: 'SUNNADE PINTATSU'.

BACKGROUND OF THE INVENTION

The present invention relates to a new and distinct cultivar of *Dianthus* plant, botanically known as *Dianthus×hybrida*, typically grown commercially as a potted plant and hereinafter referred to by the name 'Sunnade Pintatsu'.

The new *Dianthus* plant is a product of a planned breeding program conducted by the Inventor in Higashiomi, Shiga, Japan. The objective of the breeding program was to develop new freely branching *Dianthus* plants with large and attractive flowers.

The new *Dianthus* plant originated from a cross-pollination made by the Inventor in Higashiomi, Shiga, Japan in January, of a proprietary selection of *Dianthus×hybrida* identified as code number DI652-01, not patented, as the female, or seed, parent with a proprietary selection of *Dianthus×hybrida* identified as code number DI632-01, not patented, as the male, or pollen, parent. The new *Dianthus* plant was discovered and selected by the Inventor as a single flowering plant from within the progeny of the stated cross-pollination in a controlled greenhouse environment in Higashiomi, Shiga, Japan in February, 2010.

Asexual reproduction of the new *Dianthus* plant by terminal cuttings propagated in a controlled greenhouse environment in Higashiomi, Shiga, Japan since February, 2010 has shown that the unique features of this new *Dianthus* plant are stable and reproduced true to type in successive generations of asexual reproduction.

SUMMARY OF THE INVENTION

Plants of the new *Dianthus* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunnade Pintatsu'. These characteristics in combination distinguish 'Sunnade Pintatsu' as a new and distinct *Dianthus* plant:

1. Upright, outwardly spreading and mounding plant habit.
2. Vigorous growth habit.
3. Freely branching habit.
4. Freely flowering habit.
5. Large single flowers with vivid red purple-colored fringed petals; flowers positioned above and beyond the foliar plane on strong peduncles.

Plants of the new *Dianthus* differ primarily from plants of the female parent selection in flower size as plants of the new *Dianthus* have larger flowers than plants of the female parent selection.

Plants of the new *Dianthus* differ primarily from plants of the male parent selection in the following characteristics:

1. Plants of the new *Dianthus* are more freely branching than plants of the male parent selection.
2. Plants of the new *Dianthus* have larger flowers than plants of the male parent selection.
3. Flowers of plants of the new *Dianthus* and the male parent selection differ in flower color as plants of the male parent selection have red-colored flowers.

Plants of the new *Dianthus* can be compared to plants of the *Dianthus* 'Kahori', not patented. In side-by-side comparisons conducted in Higashiomi, Shiga, Japan, plants of the new *Dianthus* differed from plants of 'Kahori' in the following characteristics:

1. Plants of the new *Dianthus* were larger than plants of 'Kahori'.
2. Plants of the new *Dianthus* had thicker stems than plants of 'Kahori'.
3. Plants of the new *Dianthus* had larger leaves than plants of 'Kahori'.
4. Plants of the new *Dianthus* had larger flowers than plants of 'Kahori'.
5. Plants of the new *Dianthus* and 'Kahori' differed slightly in flower color.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph at the top of the sheet comprises a side perspective view of a typical plant of 'Sunnade Pintatsu' grown in a container.

The photograph at the bottom of the sheet is a close-up view of a typical flowering plant of 'Sunnade Pintatsu'.

DETAILED BOTANICAL DESCRIPTION

Plants used in the aforementioned photographs and following observations and measurements describe plants grown during the winter in 15-cm containers in an outdoor nursery in Higashiomi, Shiga, Japan and under cultural practices typical of commercial *Dianthus* production. During the production of the plants day temperatures ranged from 12° C. to 20° C. and night temperatures ranged from 10° C. to 12° C. Plants were seven months old when the photographs and the detailed description were taken. In the following description, color references are made to The Royal Horticultural Society Colour Chart, 2007 Edition, except where general terms of ordinary dictionary significance are used.

Botanical classification: *Dianthus×hybrida* 'Sunnade Pintatsu'.

Parentage:

*Female, or seed, parent*.—Proprietary selection of *Dianthus×hybrida* identified as code number DI652-01, not patented.

*Male, or pollen, parent*.—Proprietary selection of *Dianthus×hybrida* identified as code number DI632-01, not patented.

Propagation:

*Type*.—By terminal cuttings.

*Time to initiate roots, summer*.—About ten days at temperatures of about 20° C. to 25° C.

*Time to initiate roots, winter*.—About 14 days at temperatures of about 15° C. to 25° C.

*Time to produce a rooted young plant, summer*.—About 20 days at temperatures of about 20° C. to 25° C.

*Time to produce a rooted young plant, winter*.—About 25 days at temperatures of about 15° C. to 20° C.

*Root description*.—Fine, fibrous; white in color.

*Rooting habit*.—Moderate branching; medium density.

Plant description:

*Plant and growth habit*.—Upright, outwardly spreading and mounding plant habit; broad inverted triangle; freely basal branching habit with about eleven primary lateral branches developing per plant; vigorous growth habit.

*Plant height*.—About 19.4 cm.

*Plant diameter or spread*.—About 47 cm.

*Lateral branches*.—Length: About 16.4 cm. Diameter: About 2.2 mm. Internode length: About 5.6 mm. Texture: Glabrous, moderately glaucous. Color: Close to N138B.

*Leaf description*.—Arrangement: Opposite, simple; sessile. Length: About 12.3 cm. Width: About 1.3 cm. Shape: Lanceolate. Apex: Acute. Base: Decurrent. Margin: Entire. Texture, upper and lower surfaces: Glabrous, moderately glaucous. Venation pattern: Parallel. Color: Developing leaves, upper and lower surfaces: Close to 144B. Fully expanded leaves, upper surface: Close to 137C; venation, close to 137C. Fully expanded leaves, lower surface: Close to 137D; venation, close to 144B.

Flower description:

*Flower type and habit*.—Large single flowers; flowers terminal and axillary in cymose sprays; freely flowering habit with more than 40 flowers developing per plant at one time; flowers positioned on strong peduncles above and beyond the foliar plane; flowers face mostly upright.

*Fragrance*.—Moderately fragrant; sweet, clove-like.

*Natural flowering season*.—Flowering is continuous through the summer and into the autumn in Japan; plants begin flowering about 30 to 35 days after planting.

*Flower longevity*.—Flowers last about ten days on the plant; flowers persistent.

*Flower buds*.—Length: About 2.1 cm. Diameter: About 5.8 mm. Shape: Cylindrical. Color: Close to 64A.

*Petals*.—Quantity and arrangement: About five per flower arranged in a single whorl. Length: About 4.7 cm. Width: About 2.9 cm. Shape: Fan-shaped. Apex: Praemorse, fringed appearance. Base: Acute. Margin: Dentate to entire. Texture, upper and lower surfaces: Smooth, glabrous; towards the base, pubescent. Color: When opening, upper surface: Close to N66A. When opening, lower surface: Close to 68A. Fully opened, upper surface: Close to N66B; towards the base, close to 145C. Fully opened, lower surface: Close to 68A; towards the base, close to 145D.

*Sepals*.—Quantity and arrangement: About five per flower fused and forming a lenticular-shaped calyx. Length: About 6.5 mm. Width: About 3.8 mm. Shape: Roughly lanceolate. Apex: Acute. Margin: Entire. Texture, upper and lower surfaces: Smooth, glabrous. Color: When opening, upper surface: Close to 138B; towards the apex, close to 64A. When opening, lower surface: Close to 144C. Fully opened, upper surface: Close to 138B; towards the apex, close to 64A. Fully opened, lower surface: Close to 137B.

*Peduncles*.—Length: About 4 cm. Diameter: About 1.5 mm. Strength: Strong. Texture: Smooth, glabrous. Color: Close to 137A.

*Reproductive organs*.—Stamens: Quantity: About ten per flower. Stamen length: About 1.7 mm. Anther length: About 1.5 mm. Anther diameter: About 0.7 mm. Anther shape: Narrowly elliptic. Anther color: Close to 165D. Pollen amount: Scarce. Pollen color: Close to 165D. Pistils: Quantity: One, bi-parted. Pistil length: About 2.2 cm. Style color: Close to NN155C. Stigma shape: Elongated, curled. Stigma color: Close to 71A. Ovary color: Close to 144B to 144C. Fruits and seeds: Fruit and seed development have not been observed on plants of the new *Dianthus*.

Disease & pest resistance: Plants of the new *Dianthus* have not been observed to be resistant to pathogens and pests common to *Dianthus* plants.

Temperature tolerance: Plants of the new *Dianthus* have been observed to tolerate temperatures ranging from about 0° C. to about 35° C.

It is claimed:

1. A new and distinct *Dianthus* plant named 'Sunnade Pintatsu' as illustrated and described.

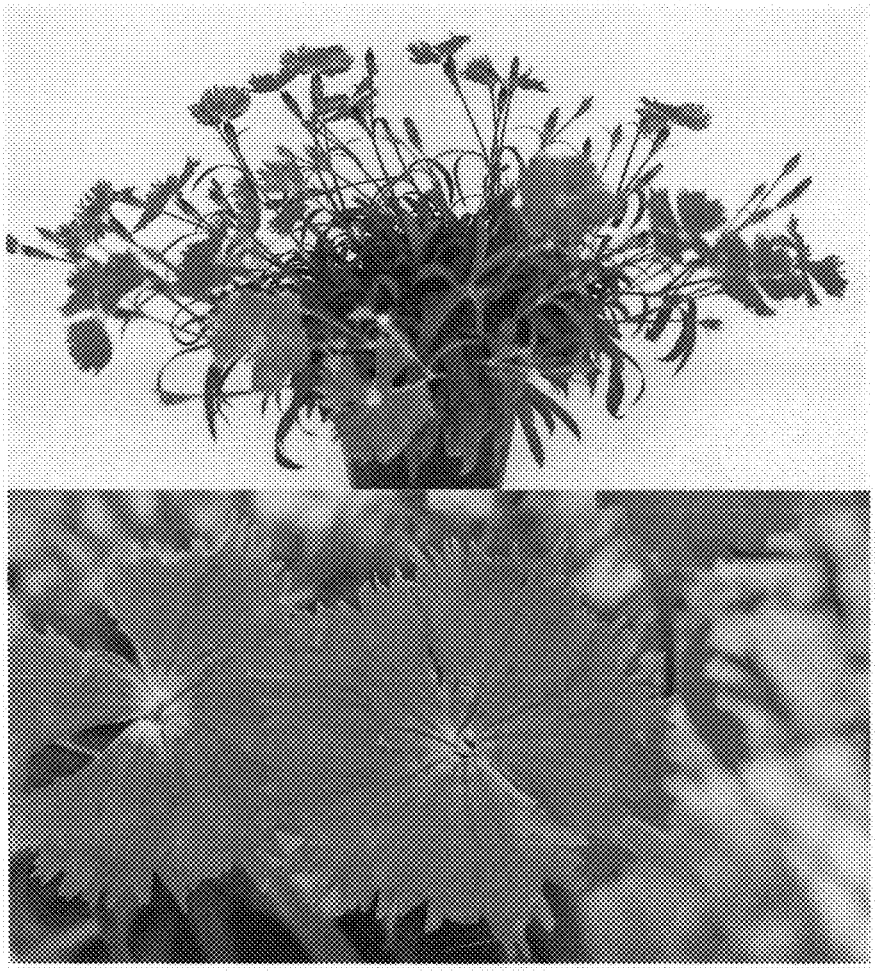

* * * * *